United States Patent [19]
Goble et al.

[11] Patent Number: 5,507,750
[45] Date of Patent: Apr. 16, 1996

[54] METHOD AND APPARATUS FOR TENSIONING GRAFTS OR LIGAMENTS

[76] Inventors: E. Marlowe Goble, 1125 Cedar Hts. Dr., Logan, Utah 84321; Richard B. Caspari, 2192 Sheppard Town Rd., Maidens, Va. 23102; W. Karl Somers, 651 North, 150 West, Logan, Utah 84321

[21] Appl. No.: 122,917

[22] Filed: Sep. 16, 1993

[51] Int. Cl.⁶ .................................................. A61B 17/56
[52] U.S. Cl. ...................... 606/102; 623/13; 73/862.391
[58] Field of Search .................. 623/13, 16; 606/99, 606/102, 105, 88, 90; 73/862.391, 862.42, 862.392

[56] References Cited

U.S. PATENT DOCUMENTS

| | | |
|---|---|---|
| Re. 34,293 | 6/1993 | Goble et al. . |
| 4,739,751 | 4/1988 | Sapega et al. ............................ 606/96 |
| 4,870,957 | 10/1989 | Goble et al. . |
| 4,950,271 | 8/1990 | Lewis et al. ............................. 606/102 |
| 4,969,895 | 11/1990 | McLeod et al. ......................... 606/96 |
| 5,037,426 | 8/1991 | Goble et al. . |
| 5,129,898 | 7/1992 | Brusasco .................................. 606/58 |
| 5,129,902 | 7/1992 | Goble et al. . |

FOREIGN PATENT DOCUMENTS 1711861   2/1992   U.S.S.R. ............................. 606/105

*Primary Examiner*—David H. Willse
*Attorney, Agent, or Firm*—Harness, Dickey & Pierce

[57] ABSTRACT

An apparatus for use in positioning a ligament or a graft within a joint during surgery. The apparatus includes a tensioning assembly which is operable to adjustably apply tension to the ligament or graft during surgery. The apparatus further includes support assembly which is operable to secure the tensioning assembly to the extremity associated with the joint. Alternatively, the tensioning assembly may be secured directly to the bone forming the joint.

18 Claims, 3 Drawing Sheets

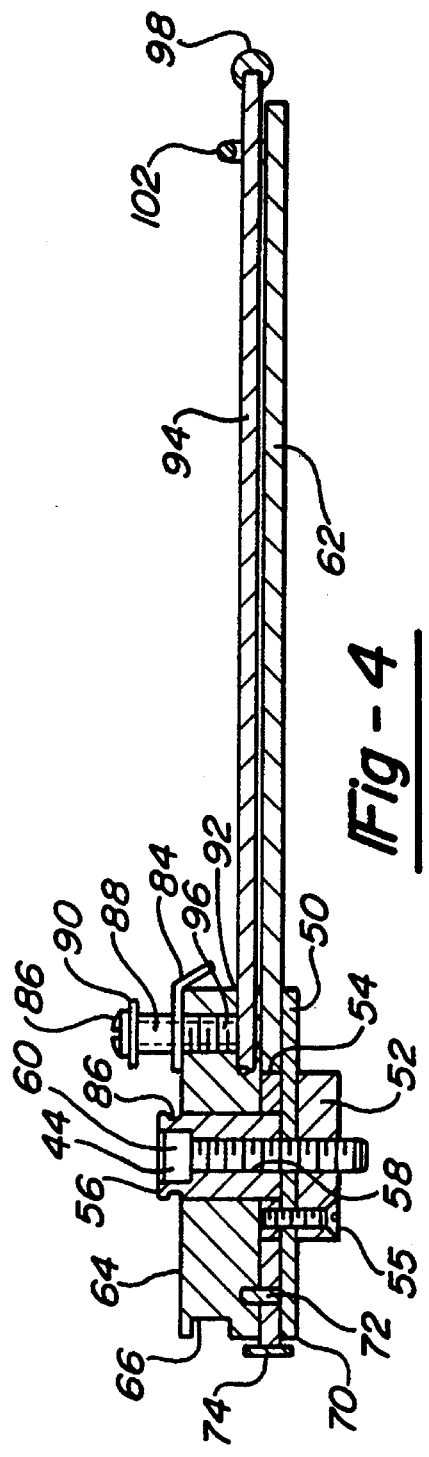
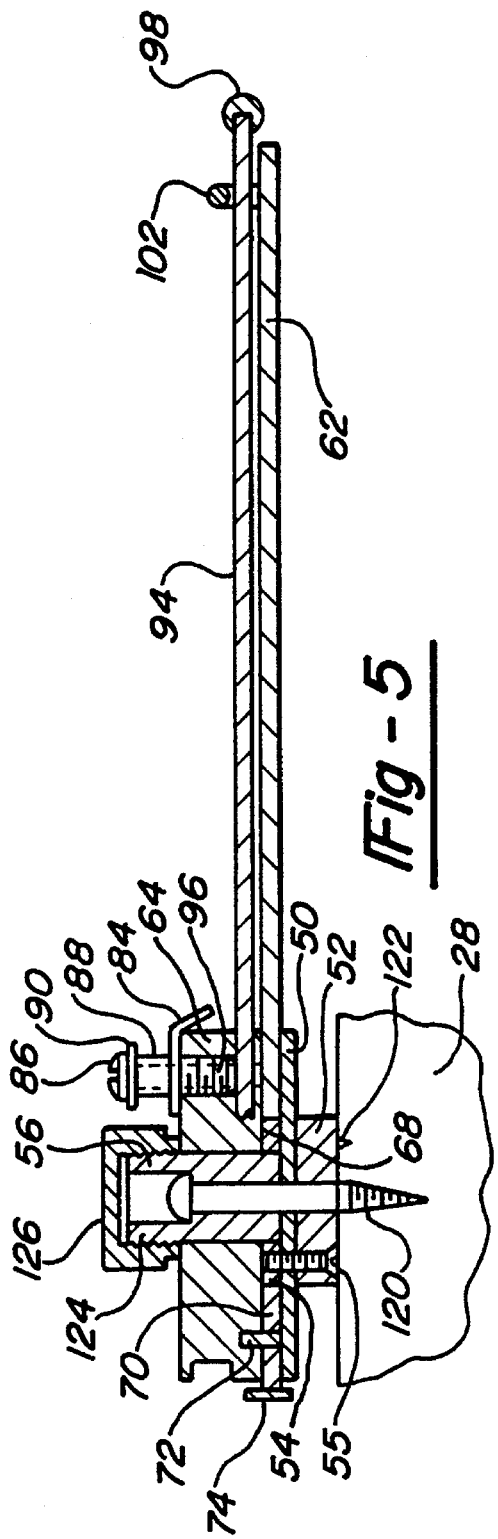

METHOD AND APPARATUS FOR TENSIONING GRAFTS OR LIGAMENTS

BACKGROUND OF THE INVENTION

1. Field of the Invention

The present invention relates generally to surgical instruments and procedures, and more particularly, to a method and apparatus for tensioning grafts or ligaments.

2. Description of the Related Art

It is well known, particularly to those who have participated in athletics, that the knee is prone to injury. Most laymen, however, consider the knee a simple hinged joint where in reality the knee provides a rather complex motion which includes not only flexion and extension, but small amounts of inward and outward rotation. In flexion and extension, the mechanical movement includes a gliding and rotation in addition to the hinging motion such that one part of the articular surface of the distal femur or proximal tibia is not always applied to the same part of the corresponding articular surface. For example, under conditions of extreme knee joint flexion, the posterior parts of the articular surfaces of the tibia have been observed to contact the femur posterior around the extremities of the condyles. If the knee where a simple hinged joint, the axis around which the revolving movement of the tibia would occur would be in the back portion of the condyle. With movement of the knee joint from flexion to semi-extension, the upper surface of the tibia will seem to glide over the condyle of the femur, such that the middle-part of the articular facets are in contact, and thus, the axis of rotation has now shifted forward to near the center of the condyle. When the knee joint is fully extended, still more gliding occurs resulting in still a further forward shift of the axis of rotation. In addition, knee joint flexure is also accompanied by a certain amount of rotation about a vertical axis drawn through the head of the tibia due to the greater length of the internal condyle and the oblique outward incline of the anterior portion of the articular surface.

The motion of the knee joint is controlled in part by the anterior and posterior cruciate ligaments (the ACL and PCL, respectively). The ACL and PCL are two very strong ligaments that cross within the knee joint and act to stabilize the knee joint movement, particularly the rotation and gliding movements described above. The ACL is attached to the anterior intercondylar area of the tibia and passes upward, backward and laterally to the lateral femoral condyle where it is attached. The PCL is attached below to the posterior intercondylar area of the tibia and passes upward, forward and medially and to the medial femoral condyle where it is attached.

The above sets forth only a brief summary of the complex nature of knee joint flexure and extension. It should, however, be apparent from the foregoing discussion that the repair of the knee ligaments, and particularly the ACL and PCL, is of significant importance to the functioning of the knee. However, surgically repairing an injury to the ligaments of the knee, and particularly the ACL and PCL, requires precise positioning and tensioning of the repair ligament. One procedure for arthroscopic repair of ligaments, and particularly the anterior and posterior cruciate ligaments, is disclosed in U.S. Pat. No. Re. 34,293 which is hereby expressly incorporated herein by reference. The procedure described in this reference provides for the precise positioning of a graft or prosthetic ligament across the knee joint. Such positioning is accomplished by forming a tunnel passing through the approximate ruptured ligament tibial and femoral points of origin and attaching a graft or prosthetic ligament therein. In addition, U.S. Pat. No. 5,037,426, which is also expressly incorporated herein by reference, discloses a method and apparatus for simply and easily verifying the isometry of the graft or prosthetic ligament. This is accomplished by securing a suture within the tunnel and measuring changes in tension in the suture as the knee joint is moved through a range of motion.

While the procedures described in the aforementioned references provide for precisely locating and verifying the position of the repair ligament across the knee joint, they do not provide a method and apparatus for setting and maintaining the tension on a graft or a ligament as it is secured across the joint. In particular, the procedure described in the U.S. Pat. No. Re. 34,293 provides only for positioning and securing a repair ligament within the knee joint as described above. The procedure disclosed in United U.S. Pat. No. 5,037,426 provides for testing the isometry of the tunnel formed in the knee joint and through which a repair ligament will be secured. The references, however, do not disclose an apparatus for tensioning the actual repair ligament as it is secured within the knee joint.

SUMMARY OF THE INVENTION

It is a principle object of the present invention to provide a method and apparatus for tensioning grafts or ligaments whereafter the surgeon may secure a graft or ligament across a joint at a desired tension.

It is another object of the present invention is to provide a method and apparatus for tensioning grafts or ligaments which is operable to eliminate pre-load and relaxation of the graft or ligament by maintaining the graft or ligament at a preset tension as the joint is taken through a range of motion during the surgical procedure.

It is still another object of the present invention to provide a method and apparatus for tensioning grafts or ligaments which is operable to maintain the graft or ligament in a tensioned position while allowing the surgeon to use a soft tissue attachment device to attach the graft or ligament to bone.

In one embodiment of the present invention, the apparatus is initially secured around the plantar aspect of the patient's foot. A tunnel is prepared beginning proximate to the tibial tuberosity and extending upward through the proximal tibial surface through the joint and into the distal femur. A repair ligament is secured in the femoral end of the tunnel and exits from the tunnel tibially. The distal end of the repair ligament is sutured and the suture material is secured to the apparatus which is then operable to set a predetermined amount of tension on the ligament and maintain this tension while the joint is exercised through its range of motion. The ligament tension is then maintained as the surgeon prepares and secures a soft tissue attachment of the ligament to the tibia.

In another embodiment of the present invention, the apparatus is secured directly to the lower tibia by means of an orthopedic screw. Ligament repair proceeds as described above, with the formation of a tunnel, securing of the repair ligament in the femur, extending the repair ligament through the tunnel exiting at the tibia and securing the repair ligament to the apparatus via sutures.

BRIEF DESCRIPTION OF THE DRAWINGS

The elements and manner of operation of the present invention, together with the further objects and advantages thereof, may best be understood by reference to the following description taken in conjunction with the accompanying drawings, in which identical reference numerals identify similar elements, and in which:

FIG. 4 is a cross-sectional view of the tensioning assembly shown in FIG. 3 taken along line 4—4 of FIG. 3; and FIG. 5 is a cross-sectional view of the tensioning assembly similar to FIG. 4 according to the second preferred embodiment of the apparatus for tensioning grafts or ligaments.

DETAILED DESCRIPTION OF THE INVENTION

The following discussion of the preferred embodiments of the present invention is merely exemplary in nature. Accordingly, this discussion in no way is intended to limit the scope of the invention, the application of the invention or the use of the invention.

Figure 1:
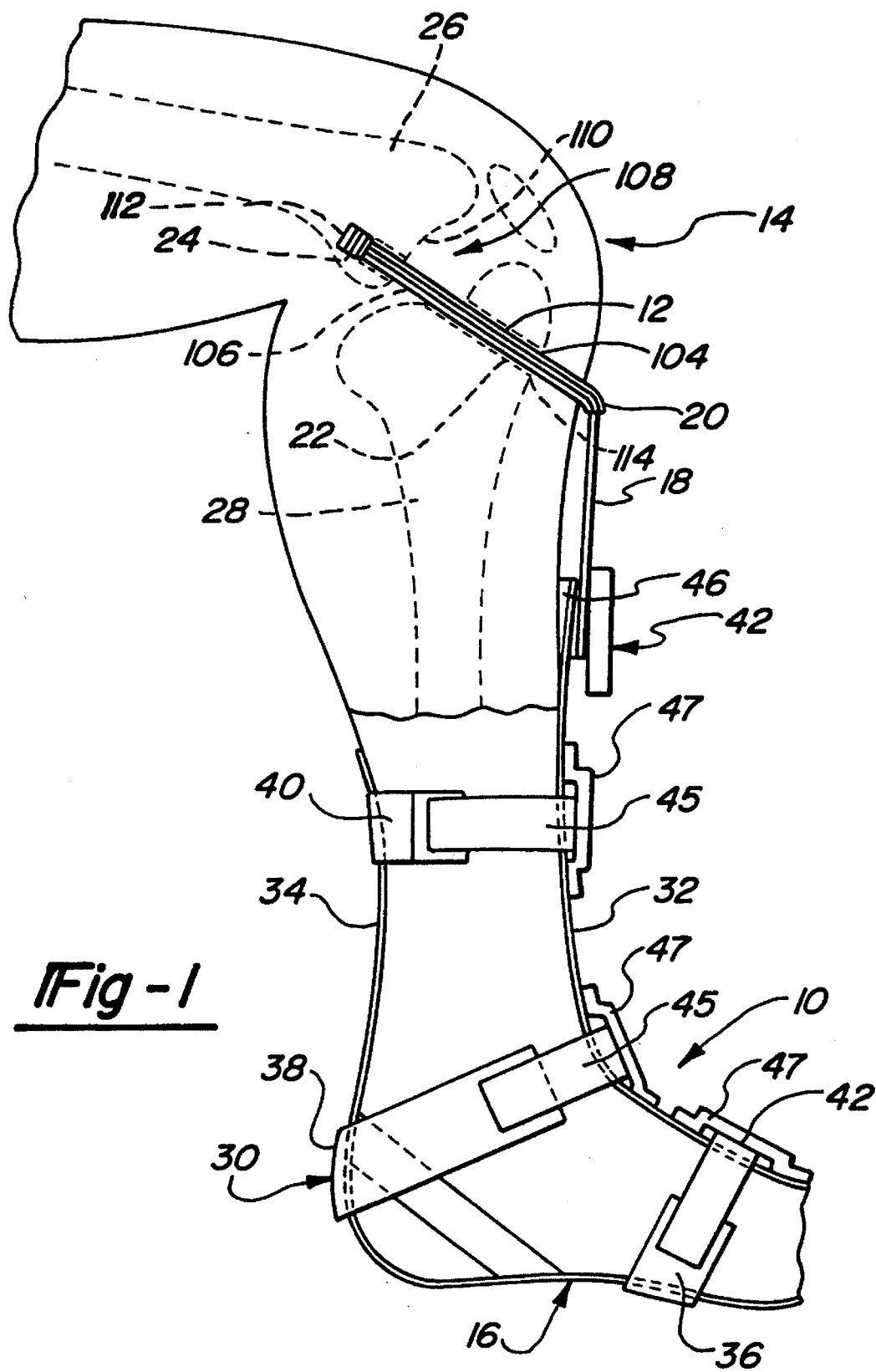
FIG. 1 is a side elevational view of a human leg in operative association with the apparatus for tensioning grafts or ligaments according to the first preferred embodiment of the present invention with the femur and tibia shown in phantom and the repair ligament shown in solid for clarity.
Figure 2:
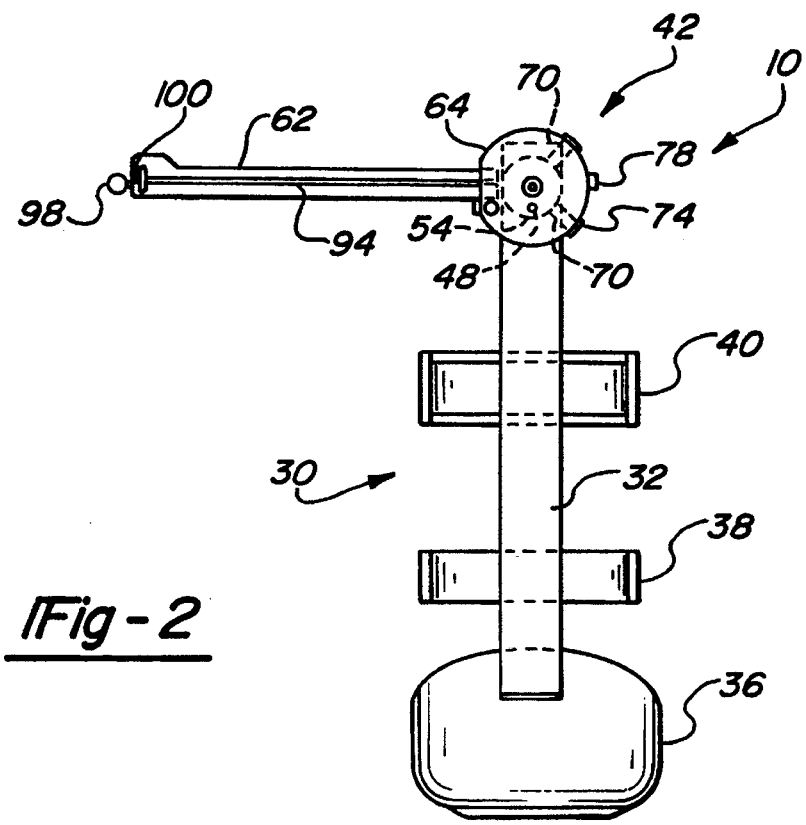
FIG. 2 is a front elevational view of the tensioning assembly shown in FIG. 1 according to the first preferred embodiment of the present invention with the retaining clamps and the clamp keepers removed.
Figure 3:
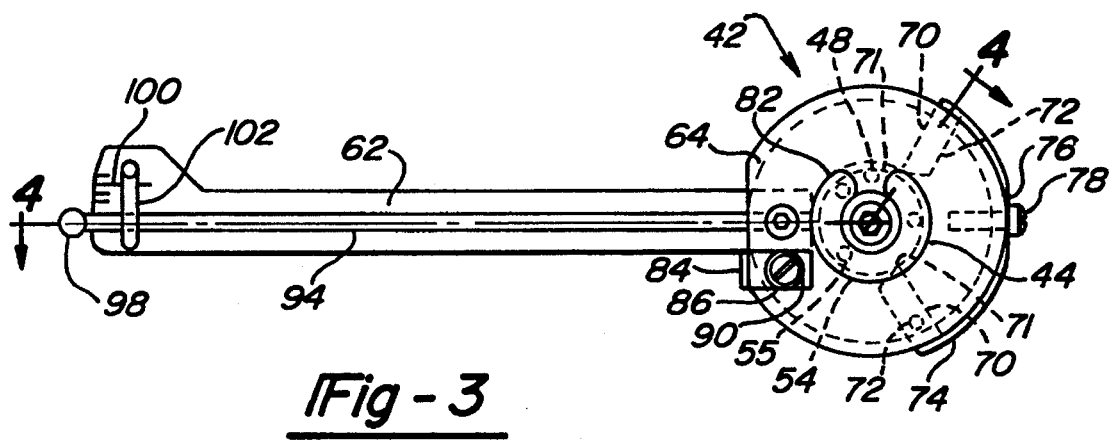
FIG. 3 is a enlarged front elevational view of the tensioning assembly of the apparatus for tensioning grafts or ligaments according to the first preferred embodiment of the present invention.

Referring to FIG. 1, an apparatus 10 for tensioning a graft 12 during a surgical repair of a knee joint 14 is shown according to the first preferred embodiment of the present invention. The graft 12 is depicted as the anterior cruciate ligament of the knee joint 14, though it is to be understood that other types of grafts or prosthetic ligaments may be used with the present invention without departing from its fair scope. The apparatus 10 is shown secured and anchored to the plantar aspect 16 of a human foot. In addition, sutures 18 are depicted as being secured both to the distal end 20 of the graft 12 as well as to the apparatus 10. The remaining portion of the graft 12 passes through the repair tunnel 22 and the proximal end 24 of the graft 12 is secured in the femur 26. In this arrangement, the apparatus 10 may be used to apply and maintain a predetermined amount of tension to the graft 12 as the surgeon, using a soft tissue attachment device (not shown), secures the distal end of the graft 12 to the tibia 28.

The apparatus 10 according to the first preferred embodiment of the present invention will now be described in greater detail. To provide means for securing the apparatus 10 at a position proximate to the knee joint 14 during surgery, the apparatus 10 comprises a stirrup assembly 30. The stirrup assembly 30 includes front and rear contoured plate members 32 and 34, respectively which are shaped to correspond to the dimensions of a typical human foot and thus would be constructed in various sizes. A plurality of straps 36, 38 and 40 are also provided and are secured to the rear contoured plate 34. The straps 36, 38 and 40 extend about the dorsal portion of the foot, the ankle and the lower leg, respectfully. A plurality of clamps 45 are provided for securing the straps 36, 38 and 40, and hence, the front and rear contoured plates 32 and 34 to the plantar aspect of the foot. The front and rear contoured plates 32 and 34 and the straps 36, 38 and 40 are formed from stainless steel material with straps 36, 38 and 40 being similarly shaped to correspond to a typical human foot. Suitable clamps are Burton Snow Board Clamps Part Nos. 328346 or 228305 which are readily available publicly. A plurality of clamp keepers 47 are also provided and secured to the front contoured plate 32 for retaining clamps 45 thereto.

To provide means for adjustably applying a tension to the graft 12 during surgery, the apparatus 10 further comprises a tensioning assembly 42. The tensioning assembly 42 is secured to an upper portion of the front contoured plate 32 by a threaded fastener 44 which engages a threaded aperture formed in the front contoured plate 32 and a mounting plate 46. A pin 48 is also provided which engages a complementary aperture formed in the front contoured plate 32 for preventing rotation of the tensioning assembly 42.

The tensioning assembly 42 includes a backing plate 50 to which a mounting spacer 52 and a ratchet wheel 54 are secured by a plurality of threaded fasteners 55. The ratchet wheel 54 is formed with 45° notches spaced at 6° intervals about its circumference. Secured to the backing plate 50 by a suitable means such as by welding is shaft 56. The shaft 56 is formed with a central axial bore 58 which includes a counter bore 60 and through which threaded fastener 44 extends for retaining tensioning assembly 42 to the front contoured plate 32. Further secured to the backing plate 52 is calibration arm 62 which extends radially outwardly from the backing plate 52.

Journally disposed about the shaft 56 is a tension wheel 64. The tension wheel 64 is formed with a recessed portion 66 into which sutures 18 are wrapped prior to being secured to the tension wheel 64 as will be described. The inner surface 68 of the tension wheel 64 is in abutting engagement with calibration arm 62 and with a pair of ratchet dogs 70. The ratchet dogs 70 are disposed between the backing plate 50 and the tension wheel 64 and are further pivotally mounted to the tension wheel 64 via the pins 72. The ratchet dogs 70 include the points 71 which are maintained in engagement with the ratchet wheel 54 by a leaf spring 74 bearing against the opposite end of the ratchet dogs 70. The leaf spring 74 is secured into a notch 76 formed in the tension wheel 64 by a threaded fastener 78. The shaft 56 is formed with a groove 80 into which a retaining clip 82 is received to retain the tension wheel 64 against the calibration arm 62 and the ratchet dogs 70. The tension wheel 64 further includes a suture tie-off clip 84 which is retained to and displaced from the tension wheel 64 by threaded fastener 86, a sleeve member 88, and a washer 90.

The tension wheel 64 is also formed with a radial bore 92 into which a deflection beam 94 is received and retained by a set screw 96. When assembled to the shaft 56, the tension wheel 64 is positioned such that the deflection beam 94 is aligned with the calibration arm 62. The deflection beam 94 further includes a knob 98 welded to its end for allowing a surgeon to apply a force thereto. The deflection beam 94 has a circular cross-section and is calibrated in diameter, length and yield strength to provide a known tension to the sutures 18 in response to a pre-determined amount of deflection. In the preferred embodiment, the deflection beam 94 is approximately 0.140 inch in diameter, 5.0 inches long, and has a yield strength in excess of 80,000 pounds per square inch. The calibration arm 62 includes a scale 100 to provide visual indication to the surgeon as to the amount of tension applied to sutures 18 and hence to the graft 12. In addition, the calibration arm 62 includes a bail 102 to prevent excessive movement of the deflection beam 94 and hence over tensioning of the graft 12. It should be appreciated that the scale 100 is only one way to indicate the amount of force applied. Other means such as electronic measuring means with, for example, LED display of the force can be used without departing from the fair scope of the present invention. For example, a piezoelectric load cell may be adapted to tensioning assembly 42 for measuring of force applied to the ligament with the output of such a device being displayed on a calibrated monitor. Other mechanical means for displaying the amount of force applied includes a spring scale type device adapted to tensioning assembly 42.

Application of force to the knob 98 of deflection beam 94 causes a rotation of the tension wheel 64 with respect to the backing plate 52 and likewise with respect to the ratchet wheel 54. The ratchet dogs 70 engage the notches formed in the ratchet wheel 54 and hence prevents the tensioning wheel 64 from returning to its unloaded position. Accordingly, once the sutures 18 are tensioned by application of force to the knob 98 of deflection beam 94, the tension on sutures 18 is maintained. The ratchet dogs 70 are spaced such that the points 71 are spaced approximately 117° apart. With this arrangement, and in conjunction with the 6° spacing of the notches of the ratchet wheel 54, only one of the ratchet dogs 70 is able to engage the ratchet wheel 54 at a time. Accordingly, the tension wheel 64 need only rotate 3 degrees before the next ratchet dog 70 engages the ratchet wheel 54.

The method of the present invention will now be described. The knee joint 14 is initially prepared in a manner similar to that disclosed in U.S. Pat. Nos. Re. 34,293 and 5,037,426. That is, the tunnel 22 is prepared beginning proximate to the tibial tuberosity 104 and extending upward through the proximal tibial surface 106 through the joint 108 and into the distal femur 110. A graft 12, either a biological graft or prosthetic ligament, is secured in the femoral end 112 of the tunnel 22 via a suitable anchoring device several of which are disclosed in U.S. Pat. No. Re. 34,293 and U.S. Pat. Nos. 4,870,957 and 5,129,902 which are hereby expressly incorporated herein by reference. The graft 12 then exits from the tunnel 22 at tibia opening 114. The distal end 20 of the graft 12 is sutured and the sutures 18 is secured to the tensioning wheel 64 at the suture tie-off 84. The sutures 18 is then drawn tight but it is not tensioned.

When the surgeon applies a force to the deflection beam 94, the sutures 18 and hence the graft 12 are drawn into tension. Moreover, the ratchet dog points 71 operate to engage the notches of the ratchet wheel 54 to maintain the tension on the graft 12. Thereafter, the surgeon may manipulate the knee joint through its range of motion to verify that the proper amount of tension has been applied to graft 12. If the tension appears to be satisfactory, the surgeon then secures the distal end of the graft 12 to the tibia 28 with a suitable soft tissue attachment device. The sutures 18 are then released from suture tie-off 84 and from the distal end of graft 12. The apparatus 10 may then be removed from the patient and the surgery completed.

The second preferred embodiment of the apparatus 10 of the present invention will now be described with reference to FIG. 5. In this embodiment, the tensioning assembly 42 is attached directly to the tibia 28 of the patient. In this regard, the threaded fastener 44 associated with the first preferred embodiment of the present invention is replaced with an appropriate orthopedic screw 120 which is driven directly into the tibia 28. In addition, the spacer 52 is formed with a plurality of barbs 122 which further engage the tibia 28 for preventing rotation of the apparatus 10. The shaft 56 is further formed with threads 124 at its second end for receiving a threaded retaining nut 126 which allows access to the orthopedic screw 120 and also retains the apparatus 10 together while providing for disassembling of the apparatus 10 for cleaning and sterilization. The apparatus 10, once secured to the patient, functions in a manner similar to that described above.

Specific embodiments of the present invention have been shown and described in detail to illustrate the principles of the present invention. The present invention may be used in various surgical procedures which are not arthroscopic in nature or related to repair of the ligaments of the knee. In this regard, the present invention may be used in conjunction with surgery on different joints as well as with other types of grafts and/or ligaments. Accordingly, it will be understood that the invention may be embodied in other forms without departing from such principles and the fair scope of the present invention.

What is claimed is:

1. An apparatus for use in positioning a ligament a joint of a patient during surgery, said apparatus comprising:

means for adjustably applying tension to the ligament so as to position the ligament during surgery; and means for noninvasively securing said means for adjustably applying tension to the ligament at position on the patient proximate to the joint, whereby the apparatus is operable to noninvasively apply tension to the ligment.

2. The apparatus for use in positioning a ligament as set forth in claim 1, wherein said means for adjustably applying tension to the ligament is further operable to provide an indication of the magnitude of tension applied to the ligament.

3. The apparatus for use in positioning a ligament as set forth in claim 1, wherein said means for adjustably applying tension to the ligament is further operable to substantially maintain the tension applied to the ligament during movement of the joint during surgery.

4. The apparatus for use in positioning a ligament as set forth in claim 1, wherein the joint is associated with an extremity of a patient, said means for securing being operable to attach to said extremity said means for adjustably applying tension to said ligament.

5. The apparatus for use in positioning a ligament as set forth in claim 1, wherein said means for adjustably applying tension to the ligament includes:

tension wheel operable to apply tension to the ligament; and a beam mechanically communicating with said tension wheel, whereby movement of said beam causes rotation of said tension wheel and therefore tension to be applied to the ligament.

6. The apparatus for use in positioning a ligament as set forth in claim 5, wherein said means for adjustably applying tension to the ligament further comprises a ratchet member operable to cause said tension wheel to resist movement in at least one direction.

7. The apparatus for use in positioning a ligament as set forth in claim 5, wherein said means for adjustably applying tension to the ligament further comprises a calibration arm operable to indicate the magnitude of tension applied to the ligament by said tension wheel.

8. An apparatus for use in positioning a graft within a joint during surgery, said joint being associated with an extremity of a patient, said apparatus comprising:

a tensioning assembly configured to apply tension to the graft so as to position the graft during surgery;

a calibration arm operable to provide an indication of the magnitude of tension applied to the graft;

means for noninvasively securing said tensioning assembly on the patient proximate to the joint; and whereby said tensioning assembly is operable to noninvasively apply tension to the graft during flexion of the joint.

9. The apparatus for use in positioning a graft as set forth in claim 8, further comprising a stirrup assembly for securing said tensioning assembly to the extremity of the patient.

10. The apparatus for use in positioning a graft as set forth in claim 8, wherein said tensioning assembly further comprises:

a tension wheel for applying tension to the graft upon rotation thereof;

a ratchet wheel mechanically communicating with said tension wheel; and a plurality of ratchet dogs pivotally mounted with respect to said tension wheel and being engageable with said ratchet wheel, said ratchet dogs being operable to limit rotation of said tension wheel to a first direction, whereby tension is applied to the graft when said tension wheel is rotated in said first direction.

11. The apparatus for use in positioning a graft as set forth in claim 10, wherein said tensioning assembly further comprises a deflection beam mechanically communicating with said tension wheel and being operable to cause rotation of said tension wheel.

12. The apparatus for use in positioning a graft as set forth in claim 11, wherein said tensioning assembly further comprises a scale cooperating with said calibration arm to indicate the magnitude of tension applied to the graft.

13. A method for tensioning a ligament within a joint of a patient during surgery, said joint being associated with an extremity of the patient and said ligament having first and second ends, said method comprising the steps of:

noninvasively securing a tensioning assembly to the patient in a region proximate to said joint;

securing said first end of said ligament to the patient;

securing said second end of said ligament to said noninvasive tensioning assembly; and applying tension to said ligament by operation of said noninvasive tensioning assembly, whereby said noninvasive tensioning assembly is operable to noninvasively apply tension to the ligament.

14. The method for tensioning a ligament as set forth in claim 13, further comprising the additional step of substantially maintaining the tension applied to said ligament during flexion of said joint during surgery.

15. The method for tensioning a ligament as set forth in claim 13, wherein said step of securing a tensioning assembly to the patient comprises the step of attaching said tensioning assembly to the extremity associated with the joint.

16. The method for tensioning a ligament as set forth in claim 13, further comprising the additional step of providing a visual indication of the magnitude of tension applied to said ligament.

17. The method for tensioning a ligament as set forth in claim 16, wherein the tensioning assembly further comprises a calibration arm, such step of providing a visual indication of the magnitude of tension applied to said ligament includes the step of allowing said calibration arm to move in response to the tension applied to said ligament.

18. The method for tensioning a ligament as set forth in claim 13, wherein said tensioning assembly comprises a tension wheel operable to apply tension to said ligament and a beam mechanically communicating with said tension wheel, said method comprising the additional step of moving said beam so as to cause rotation of said tension wheel to thereby cause tension to be applied to said ligament.

* * * * *